United States Patent [19]

Tasaka et al.

[11] 4,032,581

[45] June 28, 1977

[54] METHOD FOR SEPARATION OF M- OR P-CRESOL

[75] Inventors: Akira Tasaka, Takatsuki; Hirokazu Hosaka, Hirakata; Iwao Dohgane, Ashiya, all of Japan

[73] Assignee: Sumitomo Chemical Company, Limited, Japan

[22] Filed: July 3, 1975

[21] Appl. No.: 592,935

[30] Foreign Application Priority Data

July 12, 1974 Japan .............................. 49-80662

[52] U.S. Cl. ...................... 260/621 B; 260/627 G
[51] Int. Cl.$^2$ .................. C07C 39/06; C07C 37/22
[58] Field of Search ........ 260/621 B, 624 A, 627 G

[56] References Cited

UNITED STATES PATENTS

| 2,382,142 | 8/1945 | Engel | 260/621 B |
| 2,622,114 | 12/1952 | Carney | 260/621 B |
| 3,382,287 | 5/1968 | Fleischer et al. | 260/621 B |

*Primary Examiner*—James O. Thomas, Jr.
*Assistant Examiner*—W. B. Lone
*Attorney, Agent, or Firm*—Birch, Stewart, Kolasch and Birch

[57] ABSTRACT

A method for separating m- or p-cresol from a mixture of m- and p-cresols having a composition outside the two compositions which give respectively the eutectic points, characterized by subjecting the mixture to a crystallization treatment under a pressure of not less than about 300atmospheres.

22 Claims, No Drawings

METHOD FOR SEPARATION OF M- OR P-CRESOL

The present invention relates to a method for separation of m- or p-cresol from a mixture of m- and p-cresols (hereinafter referred to as "m- and p-cresol mixture"). More particularly, it relates to a method for separating m- or p-cresol from a m- and p-cresol mixture by subjecting the mixture to a crystallization treatment under a highly elevated pressure.

For separation of m- or p-cresol from a m- and p-cresol mixture, there are known several methods. For example, the treatment of such a mixture with urea, sodium acetate, oxalic acid or the like makes it possible to separate m- or p-cresol in the adduct form. This method has however various disadvantages: for example, it requires a large amount of solvent thus causing a problem of environmental pollution; and it needs a troublesome operation and a large scale equipment for adduct-formation and decomposition.

Further, for example, a m- and p-cresol mixture may be subjected to crystallization under atmospheric pressure such as recrystallization or sweating crystallization to give m- or p-cresol. In view of the melting points of cresols (i.e. m-cresol, 11° C; p-cresol, 34° C), it does not seem to be difficult to obtain m- or p-cresol of high purity. Actually, a great difficulty is encountered in performance of such method, because the cresols have an extremely high viscosity at low temperatures and form very fine crystals of poor filterability, thus casing difficult separation. Further, repetition of washing or sweating for enhancement of the purity of m- or p-cresol to be recovered results in a extreme decrease of the yield.

In the course of extensive studies, attention was drawn to the phenomenon that the melting points of cresols increase with an elevation of pressure. With the utilization of such phenomenon, it has now been found that m- or p-cresol of high purity is obtainable in a high efficiency and with ease from a m- and p-cresol mixture having a certain composition by subjecting the mixture to a crystallization treatment under a highly elevated pressure.

According to the present invention, there is provided a method for separation of m- or p-cresol from a m- and p-cresol mixture which comprises subjecting the mixture to a crystallization treatment under a pressure of not less than about 300 atmospheres, the mixture having a composition outside the two compositions which give respectively the eutectic points inherent to a m- and p-cresol mixture.

More specifically, this invention provides a method for obtaining m- or p-cresol of high purity from a m- and p-cresol mixture having a m- or p-cresol content higher than that in a composition giving a m- or p-rich side eutectic point, characterized by (1) applying a pressure of not less than about 300 atmospheres to the mixture charged to the first pressure-zone, thereby separating said mixture into a crystal fraction containing m- or p-cresol and a liquid fraction, (2) transferring the liquid fraction to a second pressure-zone kept under a lower pressure than that of the first pressure-zone, (3) liquefying the crystal fraction in the first pressure-zone by raising the temperature or reducing the pressure and (4) discharging the liquefied crystal fraction out of the first pressure-zone.

A m- and p-cresol mixture is known to afford two eutectic points which are constant under a fixed pressure. For instance, the eutectic points under atmospheric pressure are respectively given by the mixtures of m- and p-cresols in a molar ratio of 88:12 and 35:65, which may be referred to as "eutectic mixture(s)". Any composition which is outside the two compositions respectively affording the eutectic points may be used as the starting material in the method of the present invention. In other words, any m- and p-cresol mixture having a m-cresol content higher than the m-cresol content in the m-cresol side eutectic mixture (hereinafter referred to as "m-rich cresol") or a p-cresol content higher than the p-cresol content in the p-cresol side eutectic mixture (hereinafter referred to as "p-rich cresol") may be subjected to the crystallization treatment in this invention.

Since the eutectic points as well as the compositions affording such eutectic points are changed to some extent with the variation of pressure, the proportion of m- and p-cresols in a m- and p-cresol mixture to be treated according to the method of the invention may be varied appropriately depending upon the pressure under which the treatment is carried out. Practically and usually, however, the m-cresol content in the m-rich cresol and the p-cresol content in the p-rich cresol may be respectively from about 90 to 95 % by weight and from about 70 to 95% by weight.

Impurities usually contained in a m- and p-cresol mixture such as phenol, xylenol, methyl acetophenone and dimethylstyrene do not exert any serious influence upon the accomplishment of the method of the invention, and their presence up to about 10% by weight is usually permissible. by The method of the present invention can be carried out by charging a m- and p-cresol mixture into a pressure-vessel in the presence or absence of a solvent and increasing the pressure gradually at a pre-determined temperature. Crystallization of m- or p-cresol begins at a certain pressure, and the amount of crystals increases with the increase of pressure. After the crystallization of m- or p-cresol is completed, the uncrystallized liquid fraction is removed to separate it from the crystal fraction. Then, the remaining crystal fraction is liquefied y elevating the temperature or reducing the pressure, and the liquefied fraction is taken out to give m- or p-cresol of high purity. When solvent is contained in the liquefied fraction or the uncrystallized liquid fraction, it may be removed, for example, by distillation.

As the solvent, there may be used any organic solvent which can dissolve m- or p-cresol, has a lower melting point than the melting points of the cresols and is easily separable from the cresols, for example, by distillation. Examples of the solvent include n-hexane, n-heptane, cyclohexane, toluene, xylene, chlorobenzene, methanol, ethanol, isopropyl ether, methyl ethyl ketone, methyl isobutyl ketone, ethyl acetate, isopropyl acetate, etc. The amount of the solvent may be generally from about 3 to 40% by weight, preferably from about 3 to 15% by weight, based on the m- and p-cresol mixture. The purity of m- or p-cresol often increases as the amount of the solvent increases, but the required pressure tends to become higher.

The treating condition may suitably be selected depending on the composition of the m- and p-cresol mixture, the presence or absence of the solvent, the impurity content, etc. Generally, the temperature is in a range from about 0° to 100° C, preferably from about 30° to 80° C. The pressure is in a range from about 300 to 10,000 atmospheres, preferably from about 1,000 to 3,000 atmospheres. When the pressure is less than the above-mentioned pressure, crystallization can not sufficiently be carried out. On the other hand, higher pressures require more heavily equipped reaction vessels which are economically disadvantageous. Therefore, it is most desirable to control the temperature so that the crystallization operation may be carried out under a pressure of not more than about 3,000 atmospheres.

It sometimes occurs that separation of crystals is delayed because of the saturation phenomenon, and in this case the separation can be promoted by adding substances which can become a nucleus of crystals such as glass wool.

The purity of m- or p-cresol separated can be increased by repetition of the crystallization treatment. Such multi-stage operation is particularly effective when the purity of the m- or p-cresol is low. In the multi-stage operation, the treating condition in and after the second stage is generally milder than that of the first stage.

Increase of the purity of m- or p-cresol can similarly be achieved by reducing the pressure adiabatically after crystallization under a high-pressure and removal of the uncrystallized liquid fraction, thereby melting a part of the remaining crystal fraction and washing out the melt together with any impurities contained therein.

This operation is based on the same idea as sweating crystallization. But, in the sweating crystallization procedure wherein crystals are heated from the outside, over-melting and insufficient melting are apt to occur, and an efficient treatment is carried out only with difficulty. In the adiabatic reduction of pressure, a uniform reduction of pressure is achieved, thus enabling uniform melting throughout the crystal surface. Therefore, an increase in the purity of the cresol can be carried out efficiently.

According to the method of the present invention, the uncrystallized liquid fraction is removed out of the system under a high pressure so that separation of the crystal fraction therefrom is accomplished well, thus remarkably increasing the purity of the crystals. Moreover, the crystals obtained have grown up into a sharp crystal form almost freed from inclusion or attachment of impurities, and therefore m- or p-cresol of high purity is obtainable.

While the method of the invention may be solely and independently applied to any m- and p-cresol mixture having the said limited composition, it can be efficiently utilized for separation of m- or p-cresol from a m- and p-cresol mixture without any limitation on the composition by its application in combination with any conventional separation procedure.

When, for instance, a mixture of m- and p-cresols in a molar ratio of 60:40 is used as the starting material, a very efficient separation can be achieved first by applying thereto a conventional separation procedure via the formation of an urea adduct (cf. U.S. Pat. No. 3,855,195) so as to obtain pure m-cresol and p-rich cresol including m- and p-cresols in a molar ratio of from 20:80 to 25:75, and then by treating the p-rich cresol according to the method of this invention to obtain pure p-cresol. Alternatively, the m- and p-cresol mixture may be separated first into m-rich cresol and p-rich cresol, and then each of the m-rich cresol and the p-rich cresol fractions may be subjected to the crystallization treatment according to this invention.

Further, for instance, a m- and p-cresol mixture may be treated according to a conventional alkylation (usually butylation) procedure, followed by separation of the alkylated product to give m-rich cresol, from which pure m-cresol is obtainable by application of the method of the invention thereto.

The present invention will be illustrated in more details with reference to the following examples, which are however not to be interpreted as limiting thereto. All percentages in the examples are by weight.

EXAMPLE 1

A mixture of 50 g of toluene and 1 kg of a p-rich cresol mixture containing 78.5% of p-cresol, 19.6% of m-cresol, 1.3% of phenol and 0.6% of xylenol was charged into a pressure-vessel, and the pressure was elevated to 1,800 atmospheres at 40° C. After the uncrystallized fraction was removed out of the system, the crystal fraction was melted by reducing the pressure to 300 atmospheres and taken out of the system. The crystal fraction obtained was 342 g, of which the p-cresol was 335 g and the m-cresol was 6 g. The purity of p-cresol in the crystal fraction was 98.2%. The uncrystallized fraction was 708 g, of which the p-cresol was 450 g and the m-cresol was 190 g. Recovery of p-cresol obtained as the crystal fraction was 42.7%.

EXAMPLE 2

High-pressure treatment was carried out at 40° C under 2,000 atmospheres using the same p-rich cresol mixture as used in Example 1 but without addition of any solvent, and the uncrystallized fraction was taken out of the vessel. The crystal fraction was subjected to a sweating treatment by reducing the pressure in the system gradually, and the liquid fraction obtained by melting the crystal fraction during the treatment was also removed out of the system. The sweating treatment was stopped when the pressure was reduced to 1,000 atmospheres. The temperature in the system was then raised to 50° C, and the remaining crystal fraction was completely melted by further reduction of the pressure. The molten crystal fraction taken out of the system was 308 g, of which the p-cresol was 305 g and the m-cresol was 2 g. The purity of p-cresol in the crystal fraction was 99.3%. Yield of the liquid fraction which was first taken out as the uncrystallized fraction was 572 g, of which the p-cresol was 372 g and the m-cresol was 183 g. On the other hand, the liquid fraction taken out during the sweating treatment was 120 g, of which the p-cresol was 108 g and m-cresol was 11 g. Recovery of p-cresol was 38.9%.

EXAMPLE 3

One kilogram of a m-rich cresol mixture containing 94.2% of m-cresol, 5.2% of p-cresol and, as impurity, methyl acetophenone and dimethylstyrene in a total amount of 0.6%, was subjected to high-pressure treatment at 20° C under 2,500 atmospheres. After the uncrystallized fraction was removed out of the system, the crystal fraction was melted by reducing the pressure and then taken out of the system. Thus, the cresol mixture was separated into 384 g of the crystal fraction containing 378 g of m-cresol and 5 g of p-cresol, and 616 g of the uncrystallized fraction containing 564 g of m-cresol and 47 g of p-cresol.

What is claimed is:

1. A method for obtaining m- or p-cresol in a high purity from a mixture comprising m- and p-cresols having a composition outside the two compositions which give respectively the eutectic points inherent to the mixture, which comprises (1) applying a pressure of about 300 to about 10,000 atmospheres and a temperature of about 0° to about 100° C. to the mixture charged to a first pressure-zone, thereby separating said mixture into a crystal fraction containing either m- or p-cresol and a liquid fraction, whereby the elevated pressure causes the melting points of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by raising the temperature and (4) discharging the liquefied crystal fraction out of the first pressure-zone.

2. The method according to claim 1, wherein the crystallization treatment is carried out under a pressure of from about 1,000 to 3,000 atmospheres.

3. The method according to claim 1, wherein the crystallization treatment is carried out in the presence of an organic solvent which can dissolve m- or p-cresol, has a melting point lower than the melting points of the cresols and is easily separable from the cresols by distillation, said organic solvent being selected from the group consisting of n-hexane, n-heptane, cyclohexane, toluene, xylene, chlorobenzene, methanol, ethanol, isopropyl ether, methyl ethyl ketone, methyl isobutyl ketone, ethyl acetate and isopropyl acetate.

4. The method according to claim 3, wherein the amount of the organic solvent is from about 3 to 40 % by weight based on the mixture of m- and p-cresols.

5. The method according to claim 1, wherein the mixture of m- and p-cresols is p-rich.

6. The method according to claim 5, wherein the p-cresol content in the mixture of m- and p-cresols is from about 70 to 95 % by weight.

7. The method according to claim 10, wherein the mixture of m- and p-cresols is m-rich.

8. The method according to claim 1, wherein the mixture of m- and p-cresols is p-rich and the crystal fraction obtained is p-cresol of high purity.

9. The method according to claim 8, wherein the p-cresol content in the mixture of m- and p-cresols is from about 70 to 95% by weight. pressure-zone.

10. The method according to claim 1, wherein the mixture of m- and p-cresols is m-rich and the crystal fraction obtained is high purity m-cresol.

11. The method according to claim 1, wherein said mixture contains impurities in an amount of up to about 10% by weight.

12. The method according to claim 11, wherein said impurities comprise phenol, xylenol, methyl acetophenone or dimethylstyrene.

13. The method according to claim 1, wherein said mixture contains impurities in an amount of up to about 10% by weight.

14. A method for obtaining p-cresol in a high purity from a mixture comprising m- and p-cresols having a p-cresol content higher than that in a composition in which p-cresol predominates and which gives a eutectic point, which comprises (1) applying a pressure of about 300 to about 10,000 atmospheres and a temperature of about 0° C. to about 100° C. to the mixture charged to a first pressure-zone, thereby separating said mixture into a crystal fraction containing p-cresol and a liquid fraction, whereby the elevated pressure causes the melting points of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by raising the temperature and (4) discharging the liquefied crystal fraction out of the first pressure-zone 15. A method for obtaining m-cresol in a high purity from a mixture comprising m- and p-cresols having a m-cresol content higher than that in a composition in which m-cresol predominates and which gives a eutectic point, which comprises (1) applying a pressure of about 300 to about 10,000 atmospheres and a temperature of about 0° C. to about 100° C. to the mixture charged to a first pressure-zone, thereby separating said mixture into a crystal fraction containing m-cresol and a liquid fraction, whereby the elevated pressre causes the melting points of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by raising the temperature and (4) discharging the liquefied crystal fraction out of the first pressure-zone.

16. A method for obtaining m- or p-cresol in a high purity from a mixture comprising m- and p-cresols having a composition outside the two compositions which give respectively the eutectic points inherent to the mixture which comprises (1) applying a pressure of about 300 to about 10,000 atmospheres and a temperature of about 0° C. to about 100° C. to the mixture charged to a first pressure-zone, thereby separating said mixture into a crystal fraction containing either m- or p-cresol and a liquid fraction, whereby the elevated pressure causes the melting points of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by reducing the pressure therein and (4) discharging the liquefied crystal fraction out of the first pressure-zone.

17. The method according to claim 16, wherein the mixture of m- and p-cresols is p-rich and the crystal fraction obtained is p-cresol of high purity.

18. The method according to claim 17, wherein the p-cresol content in the mixture of m- and p-cresols is from about 70 to 95% by weight.

19. The method according to claim 16, wherein the mixture of m- and p-cresols is m-rich and the crystal fraction obtained is high purity m-cresol.

20. The method according to claim 16, wherein said mixture contains impurities in an amount of up to about 10% by weight.

21. A method for obtaining p-cresol in a high purity from a mixture comprising m- and p-cresols having a p-cresol content higher than that in a composition in which p-cresol predominates and which gives a eutectic point, which comprises applying a pressure of about 300 to about 10,000 atmospheres and a temperature of about 0° C. to about 100° C. to the mixture charged to a first pressure-zone, thereby separating said mixture into a crystal fraction containing p-cresol and a liquid fraction, whereby the pressure causes the melting point of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by reducing the pressure and (4) discharging the liquefied crystal fraction out of the first pressure-zone.

22. A method for obtaining m-cresol in a high purity from a mixture comprising m- and p-cresols having a m-cresol content higher than that in a composition in which m-cresol predominates and which gives a eutectic point, which comprises applying a pressure of about 300 to about 10,000 atmospheres and a temperature of about 0° C. to about 100° C. to the mixture charged to a first pressure-zone, thereby separating said mixture into a crystal fraction containing m-cresol and a liquid fraction, whereby the elevated pressure causes the melting points of the m-cresol and p-cresol to be raised above that obtained under atmospheric pressure, (2) transferring said liquid fraction to a second pressure-zone kept under a lower pressure than that of the first pressure-zone, said lower pressure being sufficient to enable transfer of the liquid fraction from said first pressure-zone to said second pressure-zone, (3) liquefying the crystal fraction remaining in the first pressure-zone by reducing the pressure and (4) discharging the liquefied crystal fraction out of the first pressure-zone.

* * * * *